United States Patent
Ohmiya et al.

(10) Patent No.: US 9,903,864 B2
(45) Date of Patent: Feb. 27, 2018

(54) SAMPLE ANALYSIS TOOL, METHOD FOR PRODUCING SAMPLE ANALYSIS TOOL, AND METHOD FOR INHIBITING DECREASE IN LIQUID PERMEABILITY OF DEVELOPMENT MEMBER

(75) Inventors: Kazuhiro Ohmiya, Kyoto (JP); Tomoko Hirayama, Kyoto (JP)

(73) Assignee: Arkray, Inc., Kyoto (JP)

( * ) Notice: Subject to any disclaimer, the term of this patent is extended or adjusted under 35 U.S.C. 154(b) by 115 days.

(21) Appl. No.: 13/263,729

(22) PCT Filed: Apr. 5, 2010

(86) PCT No.: PCT/JP2010/056187
§ 371 (c)(1),
(2), (4) Date: Oct. 7, 2011

(87) PCT Pub. No.: WO2010/116979
PCT Pub. Date: Oct. 14, 2010

(65) Prior Publication Data
US 2012/0034140 A1    Feb. 9, 2012

(30) Foreign Application Priority Data
Apr. 9, 2009    (JP) .................. 2009-094836

(51) Int. Cl.
*B01L 3/00*    (2006.01)
*B23P 11/00*    (2006.01)
(Continued)

(52) U.S. Cl.
CPC ......... *G01N 33/558* (2013.01); *G01N 33/525* (2013.01); *Y10T 29/49826* (2015.01)

(58) Field of Classification Search
CPC ................ G01N 33/558; G01N 33/525; Y10T 29/49826
See application file for complete search history.

(56) References Cited

U.S. PATENT DOCUMENTS 4,876,076 A   10/1989   Colley
5,037,736 A    8/1991   Freitag et al.
(Continued)

FOREIGN PATENT DOCUMENTS

CN         1327159 A      12/2001
CN       101078726 A      11/2007
(Continued)

OTHER PUBLICATIONS

Extended European Search Report for corresponding European Application No. 10761678.1 dated Aug. 23, 2012.
(Continued)

*Primary Examiner* — Jill Warden
*Assistant Examiner* — Julie Tavares
(74) *Attorney, Agent, or Firm* — Knobbe, Martens, Olson & Bear, LLP (57) ABSTRACT

Provide is a sample analysis tool whose reactivity and reproducibility in analysis can be prevented from decreasing. The sample analysis tool 10 of the present invention includes a development member 11 and a plastic base 16, and at least part of the development member 11 is in contact with the plastic base 16. The sample analysis tool 10 further includes a hydrophilic component layer 15, and the hydrophilic component layer 15 is formed on part or the whole of at least one of a surface of the plastic base 16 and a surface of the development member 11. It is particularly preferable that the hydrophilic component layer 15 contains sucrose or N-methyl glucosamine. In the sample analysis tool 10 of the present invention, since the hydrophilic component layer 15 is formed on part or the whole of at least one of the surface of the plastic base 16 and the surface of the development member 11, it is possible to prevent the adhesion of a hydrophobic component(s) derived from the plastic base 16.

15 Claims, 5 Drawing Sheets

(51) Int. Cl.
*G01N 33/558* (2006.01)
*G01N 33/52* (2006.01)

(56) References Cited

U.S. PATENT DOCUMENTS

| | | | |
|---|---|---|---|
| 5,223,436 A | 6/1993 | Freitag et al. | |
| 5,262,067 A | 11/1993 | Wilk et al. | |
| 5,603,898 A | 2/1997 | Ashihara et al. | |
| 5,846,359 A | 12/1998 | Ota et al. | |
| 6,022,433 A | 2/2000 | Ota et al. | |
| 6,303,081 B1 * | 10/2001 | Mink et al. | 422/412 |
| 6,399,398 B1 | 6/2002 | Cunningham et al. | |
| 2003/0092093 A1 | 5/2003 | Kitawaki et al. | |
| 2004/0101972 A1 | 5/2004 | Schoedel | |
| 2004/0248322 A1 | 12/2004 | Charlton | |
| 2005/0214951 A1 | 9/2005 | Nahm et al. | |
| 2008/0003141 A1 | 1/2008 | Iketani | |
| 2009/0053829 A1 | 2/2009 | Okamura et al. | |
| 2010/0068820 A1 | 3/2010 | Meathrel et al. | |

FOREIGN PATENT DOCUMENTS

| | | |
|---|---|---|
| CN | 101403758 A | 4/2009 |
| EP | 0310940 A2 | 4/1989 |
| EP | 0 582 231 A1 | 2/1994 |
| EP | 0 420 021 A2 | 7/1996 |
| EP | 0 810 436 A1 | 12/1997 |
| EP | 1 288 663 A1 | 3/2003 |
| EP | 1321478 A2 | 6/2003 |
| EP | 2 317 319 A1 | 5/2011 |
| JP | 64-088156 A | 4/1989 |
| JP | H01-114756 | 5/1989 |
| JP | 2703823 B2 | 9/1991 |
| JP | H05-099918 | 4/1993 |
| JP | H06-167497 A | 6/1994 |
| JP | H06-506000 | 7/1994 |
| JP | H10-177028 | 6/1998 |
| JP | H10-505909 | 6/1998 |
| JP | 2000-310639 A | 11/2000 |
| JP | 2001-083152 A | 3/2001 |
| JP | 2001-249133 A | 9/2001 |
| JP | 3438050 B2 | 6/2003 |
| JP | 2003-304868 A | 10/2003 |
| JP | 3498188 B2 | 12/2003 |
| JP | 2004-085425 A | 3/2004 |
| JP | 2004-233127 A | 8/2004 |
| JP | 2005-061910 | 3/2005 |
| JP | 2006-038600 A | 2/2006 |
| JP | 2007-218593 | 8/2007 |
| JP | 2007-524813 | 8/2007 |
| JP | 2007-248073 | 9/2007 |
| JP | 2008-116235 | 5/2008 |
| JP | 2008-519757 A | 6/2008 |
| JP | 2008-544282 | 12/2008 |
| JP | 2009-516199 A | 4/2009 |
| WO | 96/09546 A1 | 3/1996 |
| WO | 96/24062 A1 | 8/1996 |
| WO | WO 2002/040999 A1 | 5/2002 |
| WO | 03/062824 A1 | 7/2003 |
| WO | WO 2005/007698 A1 | 1/2005 |
| WO | WO 2005/106463 A1 | 11/2005 |
| WO | 2007/061793 A2 | 5/2007 |
| WO | 2010/001598 A1 | 1/2010 |

OTHER PUBLICATIONS

Fujifilm Global, Fuji Dri-Chem 4000i: History & Principle in 2 pages.
PCT International Search Report in PCT Application No. PCT/JP2010/056187 dated May 11, 2010 in 2 pages.
Office Action dated Jun. 13, 2013 in corresponding European Application No. 10761678.1.
Office Action dated Jan. 21, 2014 in corresponding European Patent Application No. 10761678.1.
Application document of Japanese Patent Application No. JP2009-086378 filed on Mar. 31, 2009.

* cited by examiner

SAMPLE ANALYSIS TOOL, METHOD FOR PRODUCING SAMPLE ANALYSIS TOOL, AND METHOD FOR INHIBITING DECREASE IN LIQUID PERMEABILITY OF DEVELOPMENT MEMBER

TECHNICAL FIELD

The present invention relates to a sample analysis tool, a method for producing a sample analysis tool, and a method for inhibiting the decrease in liquid permeability of a development member.

BACKGROUND ART

Heretofore, for example, in the diagnosis or the like of infectious diseases, sample analysis tools for detecting antigens of pathogens such as bacteria and viruses utilizing an immunoreaction are in widespread use. In such sample analysis tools, immunochromatography (hereinafter also may be referred to as an "immunoassay method") is used widely because it allows quantitative analysis, semi-quantitative analysis, qualitative analysis, or the like to be performed easily and rapidly. In recent years, an immunoassay method in which an enzyme is used as a label (hereinafter, such a method may also be referred to as an "enzyme immunoassay method") has been developed (see Patent Document 1, for example).

Figure 6A:
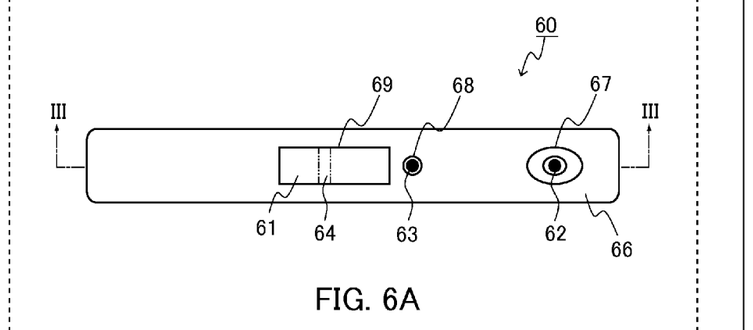
FIG. 6A is a plan view showing an example of the configuration of a conventional sample analysis tool.
Figure 6B:
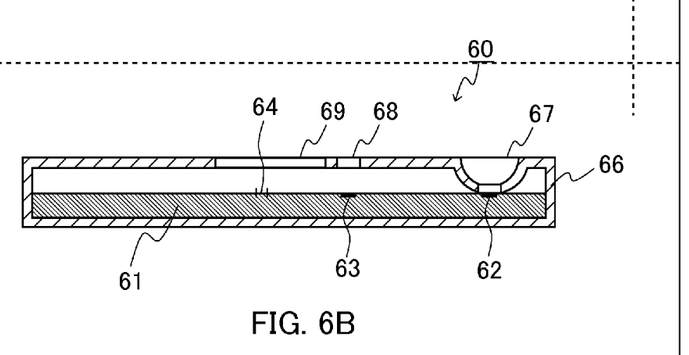
FIG. 6B is a sectional view showing the sample analysis tool, viewed along arrows III-III in FIG. 6A.

As shown in FIG. 6, a conventional sample analysis tool 60 generally is configured so that a development member 61 is contained in a plastic case 66. FIG. 6A is a plan view of the sample analysis tool. FIG. 6B is a sectional view of the sample analysis tool, viewed along arrows III-III in FIG. 6A. In FIGS. 6A and 6B, common components and portions are given the same reference numerals. In the development member 61, a developing solution supply portion 62, a sample supply portion 63, and a detection portion 64 are provided in this order from upstream to downstream along the flow of a developing solution (from the right to the left in FIGS. 6A and 6B). In the detection portion 64, an antibody is immobilized (hereinafter, the antibody may also be referred to as the "immobilized antibody"). In the plastic case 66, a developing solution supply port 67, a sample supply port 68, and a window 69 are formed. The developing solution supply port 67 is provided so that the lower end thereof is in contact with the developing solution supply portion 62. The sample supply port 68 is provided above the sample supply portion 63. The window 69 is provided above the detection portion 64.

CITATION LIST

Patent Document(s)

Patent Document 1: JP 2005-61910 A

BRIEF SUMMARY OF THE INVENTION

Problem to be Solved by the Invention

When the enzyme immunoassay method or the like is performed using a conventional sample analysis tool, a problem of decrease in reactivity, i.e., a sample that should be determined as positive is determined as negative, may occur in qualitative analysis; or a problem of decrease in reproducibility, i.e., variability is seen among quantified values, may occur in quantitative analysis, for example. Such problems occur not only in the sample analysis tools for use in an immunoassay method but also in sample analysis tools used generally in clinical tests and the like, which conduct analysis by reacting a sample solution with a reagent contained in a reagent layer, for example.

With the foregoing in mind, it is an object of the present invention to provide a sample analysis tool whose reactivity and reproducibility in analysis can be prevented from decreasing, a method for producing such a sample analysis tool, and a method for inhibiting the decrease in liquid permeability of a development member.

Means for Solving Problem

In order to achieve the above object, the sample analysis tool according to the present invention includes: a plastic base; a development member comprising a portion contacting the plastic base; and a hydrophilic component layer disposed on at least a portion of a surface of the plastic base or at least a portion of a surface of the development member.

Furthermore, the method for producing a sample analysis tool according to the present invention is a method for producing a sample analysis tool in which at least a portion of a development member is in contact with a plastic base. The method includes the step of: forming a hydrophilic component layer on least a portion of a surface of the plastic base or at least a portion of a surface of the development member.

Still further, the method for inhibiting a decrease in liquid permeability of a development member according to the present invention is a method for inhibiting a decrease in liquid permeability of a development member in a sample analysis tool comprising a development member and a plastic base, wherein the plastic base comprises a hydrophobic component, and at least a portion of the development member is in contact with the plastic base. The method includes the steps of: forming a hydrophilic component layer on at least a portion of a surface of the plastic base or at least a portion of a surface of the development member; and preventing the hydrophobic component from adhering to the development member by the hydrophilic component layer, thereby inhibiting decrease in liquid permeability of the development member.

Effects of the Invention

According to the present invention, the reactivity and reproducibility in analysis can be prevented from decreasing.

MODE FOR CARRYING OUT THE INVENTION

In order to achieve the above object, the inventors of the present invention first conducted a series of studies in order to clarify the cause of the decrease in reactivity and reproducibility in analysis in a conventional sample analysis tool. As a result, the inventors of the present invention found out the cause is that, in the conventional sample analysis tool, for example, the permeability of a development member to liquid supplied to a liquid supply portion such as a developing solution supply portion or a sample supply portion decreases. The decrease in permeability to liquid means, for example: the liquid no longer permeates the development member; it takes time for the liquid to permeate the development member; and the like. Owing to this decrease in permeability, the reactivity and reproducibility in analysis decrease. Based on this finding, the inventors of the present invention conducted further studies. As a result, they discovered that, in a sample analysis tool configured so that at least part of a development member is in contact with a plastic base, it is possible to inhibit the decrease in liquid permeability of the development member by forming a hydrophilic component layer on part or the whole of at least one of a surface of the plastic base and a surface of the development member, thereby achieving the present invention. According to the present invention, the reactivity and reproducibility in analysis can be prevented from decreasing.

The sample analysis tool of the present invention may be configured so that, for example, the hydrophilic component layer is formed on at least a portion of a contact portion of the development member contacting the plastic base.

The sample analysis tool of the present invention may be configured so that, for example, the development member includes a liquid supply portion, and the hydrophilic component layer is formed on at least a portion of a surface of the liquid supply portion. The liquid supply portion is not particularly limited, and may be a developing solution supply portion, a sample supply portion, a reagent supply portion, a cleaning solution supply portion, or the like, for example.

The sample analysis tool and the method for producing a sample analysis tool according to the present invention may be configured so that, for example, the contact portion of the development member contacting the plastic base includes the liquid supply portion.

The sample analysis tool of the present invention may be configured so that, for example, the liquid supply portion includes a developing solution supply portion and a sample supply portion, and the hydrophilic component layer is formed on at least a portion of a surface of the developing solution supply portion and or at least a portion of a surface of the sample supply portion.

In the sample analysis tool of the present invention, it is preferable that the hydrophilic component layer contains a nonvolatile hydrophilic component.

In the sample analysis tool of the present invention, it is preferable that the hydrophilic component layer contains a component(s) selected from saccharides, water-soluble polymers, surfactants, colloid particles, and inorganic particles, for example. Examples of the saccharides include sucrose, N-methyl glucosamine, glucose, fructose, maltose, and lactose. Among them, sucrose and N-methyl glucosamine are particularly preferable.

The sample analysis tool of the present invention may be configured so that, for example, the sample supply portion is configured to receive a sample solution containing a sample, and a the developing solution supply portion is configured to receive developing solution.

The sample analysis tool of the present invention may be configured so that, for example: the development member further includes a detection portion; the developing solution supply portion, the sample supply portion, and the detection portion are provided in the development member in this order from upstream to downstream along a flow of a developing solution; a substance that specifically binds to an analyte in the sample is immobilized in the detection portion; wherein the sample supply portion is configured to receive a sample solution containing a sample; wherein the developing solution supply portion is configured to receive the developing solution; wherein the supplied sample solution is introduced to the detection portion by development of the supplied developing solution in the development member in the presence of a labeled substance that specifically binds to the analyte; wherein a complex comprising the immobilized substance that specifically binds to an analyte, the analyte, and the labeled substance that specifically binds to an analyte is formed in the detection portion; and wherein the sample analysis tool is configured to analyze the analyte by detecting the label in the complex.

Each of the immobilized substance that specifically binds to the analyte and the labeled substance that specifically binds to the analyte may be selected as appropriate depending on the analyte, for example. It may be a substance derived from a living organism or a substance produced (synthesized) artificially. Examples of the specifically binding substance include antibodies, antigens, and probes.

The sample analysis tool of the present invention may be configured so that, for example, the plastic base is configured to hold the development member in a sandwiched manner.

The sample analysis tool of the present invention may be configured so that, for example, it further includes a reagent layer, and the plastic base is configured to hold the development member and the reagent layer in a sandwiched manner.

In the sample analysis tool, the method for producing a sample analysis tool, and the method for inhibiting decrease in liquid permeability of a development member according to the present invention, it is preferable that the plastic base contains a hydrophobic component. The hydrophobic component may be a lubricant, a plasticizer, a release agent, a stabilizer, an antioxidant, or the like, for example.

The method for producing a sample analysis tool according to the present invention may be configured so that, for example, in the step of forming the hydrophilic component layer, the hydrophilic component layer is formed on at least a portion of a contact portion of the development member contacting the plastic base.

The method for producing a sample analysis tool according to the present invention may be configured so that, for example: the development member includes a liquid supply portion; and in the step of forming the hydrophilic component layer, the hydrophilic component layer is formed on at least a portion of a surface of the liquid supply portion.

The method for producing a sample analysis tool according to the present invention may be configured so that, for example: the liquid supply portion includes a developing solution supply portion and a sample supply portion; and in the step of forming the hydrophilic component layer, the hydrophilic component layer is formed on at least a portion of a surface of the developing solution supply portion or at least a portion of a surface of the sample supply portion.

The method for inhibiting the decrease in liquid permeability of a development member according to the present invention may be configured so that, for example: the development member includes a liquid supply portion and at least a portion of the liquid supply portion is in contact with the plastic base; and the hydrophilic component layer is formed on at least a portion of a surface of the liquid supply portion.

The method for inhibiting the decrease in liquid permeability of a development member according to the present invention may be configured so that, for example: the liquid supply portion includes a developing solution supply portion and a sample supply portion; and the hydrophilic component layer is formed on at least a portion of a surface of the developing solution supply portion or at least a portion of a surface of the sample supply portion.

Next, the present invention will be described in detail. It is to be noted, however, the present invention is by no means limited by the following description. In FIGS. 1 to 6 to be described below, common components and portions are given the same reference numerals. In the drawings, for the sake of simplicity in illustration, the structure of each component and portion may be simplified as appropriate, and the size or the like of each component and portion may be different from the actual size or the like.

First Embodiment

A sample analysis tool according to the present embodiment is a sample analysis tool for use in an immunoassay method (enzyme immunoassay method) in which an immobilized antibody is used as the "immobilized specifically binding substance" and a labeled antibody labeled with an enzyme (an enzyme-labeled antibody) is used as the "labeled specifically binding substance".

FIG. 1 shows an example of the configuration of the sample analysis tool of the present embodiment. FIG. 1A is a plan view showing a development member included in this sample analysis tool. FIG. 1B is a sectional view of the development member, viewed along arrows I-I in FIG. 1A.

Figure 1A:
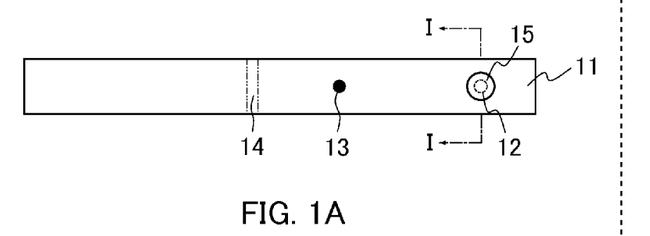
FIG. 1A is a plan view showing an example of the configuration of a development member included in a sample analysis tool according to one embodiment of the present invention.
Figure 1B:
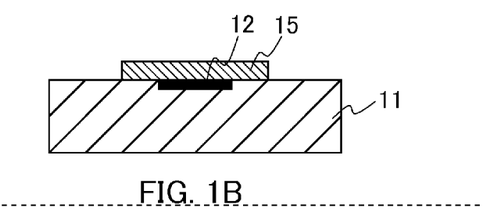
FIG. 1B is a sectional view of the development member, viewed along arrows I-I in FIG. 1A.

As shown in FIGS. 1A and 1B, on this development member 11, a developing solution supply portion 12, a sample supply portion 13, and a detection portion 14 are provided in this order from upstream to downstream along the flow of a developing solution (from the right to the left in FIG. 1A). In the present embodiment, the developing solution supply portion 12, the sample supply portion 13, and the detection portion 14 are predetermined regions in the development member 11. On a surface of the developing solution supply portion 12, a hydrophilic component layer 15 is formed so as to cover the surface of the developing solution supply portion 12 entirely. An antibody is immobilized in the detection portion 14 (immobilized antibody).

Figure 1C:
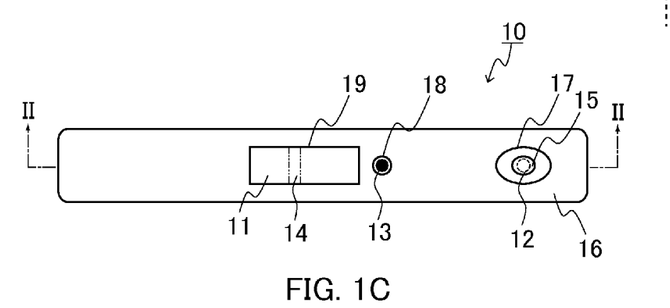
FIG. 1C is a plan view showing an example of the configuration of the sample analysis tool according to the embodiment of the present invention.
Figure 1D:
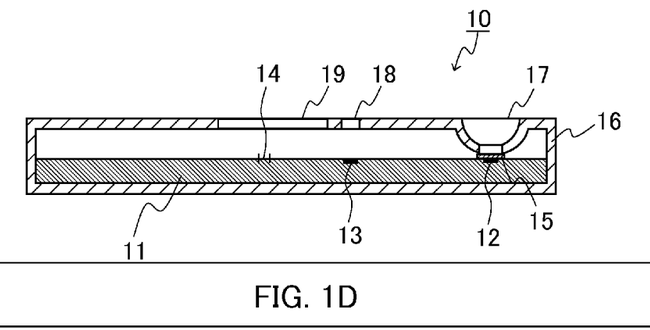
FIG. 1D is a sectional view showing the sample analysis tool, viewed along arrows II-II in FIG. 1C.

FIG. 1C is a plan view showing the sample analysis tool of the present embodiment. FIG. 1D is a sectional view showing the sample analysis tool, viewed along arrows II-II in FIG. 1C. As shown in FIGS. 1C and 1D, this sample analysis tool 10 includes the development member 11 shown in FIG. 1A and a plastic case 16 as the plastic base. The development member 11 is disposed in the plastic case 16. The plastic case 16 includes a developing solution supply port 17, a sample supply port 18, and a window 19. The developing solution supply port 17 is provided so that the lower end thereof is in contact with the hydrophilic component layer 15. The sample supply port 18 is provided above the sample supply portion 13. The window 19 is provided above the detection portion 14.

Figure 2A:
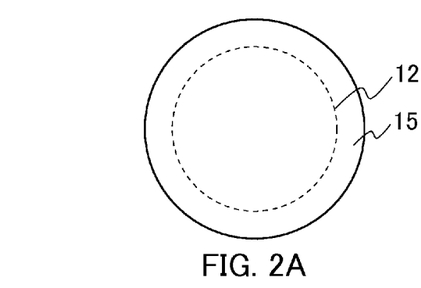
FIG. 2 shows examples of a hydrophilic component layer formed on a surface of a developing solution supply portion.
Figure 2B:
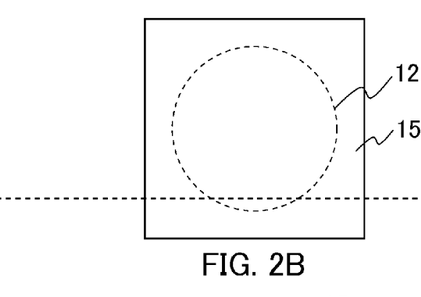
Figure 2C:
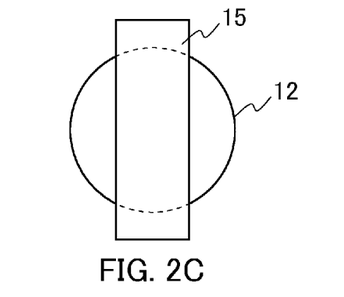
Figure 2D:
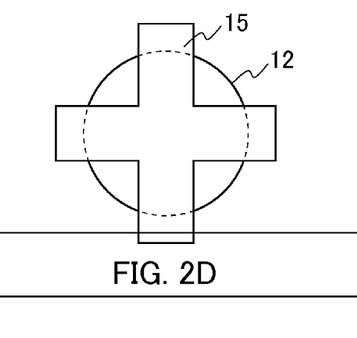

In this sample analysis tool 10, as shown in FIG. 2A, the hydrophilic component layer 15 is formed in a circular shape so as to cover the surface of the developing solution supply portion 12 entirely. It is to be noted, however, the present invention is not limited to this illustrative example. For instance, as shown in FIG. 2B, the hydrophilic component layer 15 may be formed in a rectangular shape so as to cover the surface of the developing solution supply portion 12 entirely; as shown in FIG. 2C, the hydrophilic component layer 15 may be formed in a rectangular shape so as to cover the surface of the developing solution supply portion 12 partially; or as shown in FIG. 2D, the hydrophilic component layer 15 may be formed in a cross shape so as to cover the surface of the developing solution supply portion 12 partially. In the sample analysis tool of the present embodiment, the hydrophilic component layer 15 is formed in the contact portion between the development member 11 (the developing solution supply portion 12) and the plastic case 16 (the lower end of the developing solution supply port 17). Although the lower end of the developing solution supply port 17 is in contact with the hydrophilic component layer 15, the present invention is not limited to this illustrative example. It is not always necessary that the lower end of the developing solution supply port 17 is in contact with the hydrophilic component layer 15. Furthermore, although the hydrophilic component layer 15 is formed on the surface of the developing solution supply portion 12 in this sample analysis tool 10, the present invention is not limited to this illustrative example. The hydrophilic component layer 15 may be formed on, part or the whole of the surface of the sample supply portion 13, for example. Alternatively, the hydrophilic component layer 15 may be formed so as to cover both the developing solution supply portion 12 and the sample supply portion 13, or the hydrophilic component layer 15 may be formed so as to cover the developing solution supply portion 12 and the sample supply portion 13, respectively, for example.

The development member is not particularly limited as long as it has a porous structure exhibiting a capillary action. The material forming the development member may be a porous membrane, a granular substance, particulate powder, or the like, for example. Examples of the porous membrane include: cellulose membranes; membranes formed of cellulose derivatives such as cellulose acetate and nitrocellulose; glass filters; and filter papers. Examples of the granular substance or the particulate powder include polymer beads, glass beads, titanium dioxide, cellulose, salts, and hydrophobized polysaccharides. The size of the development member is not particularly limited, and can be set as appropriate depending on the specification and the like of an analyzer, for example.

The hydrophilic component layer is not particularly limited as long as it contains a hydrophilic component(s). As described above, the hydrophilic component layer is formed on part or the whole of the surface of the developing solution supply portion. With this configuration, it is possible to inhibit the decrease in permeability to the developing solution, whereby the reactivity and reproducibility in analysis can be prevented from decreasing. It is speculated that such an effect is obtained by the following mechanism. Specifically, the permeability to the developing solution is decreased by the adhesion of a hydrophobic component(s) contained in the plastic case (e.g., a lubricant, a plasticizer, a release agent, a stabilizer, an antioxidant, or the like) to part or the whole of the surface of the developing solution supply portion. In particular, the adhesion of the hydrophobic component(s) occurs notably when the sample analysis tool is stored in a high-temperature environment (e.g., 30° C. or higher), or for a long time (e.g., 6 months or longer), for example. In the sample analysis tool of the present embodiment, the adhesion of the hydrophobic component(s) is prevented by forming the hydrophilic component layer on part or the whole of the surface of the developing solution supply portion, and as a result, the decrease in permeability to the developing solution is inhibited. It should be noted, however, the present invention is by no means limited or restricted by this speculation. Furthermore, in the present invention, the location where the hydrophilic component layer is formed is not limited only to the developing solution supply portion described above. The effect of the present invention can be obtained as long as the hydrophilic component layer is formed on part or the whole of at least one of the surface of the plastic base and the surface the development member.

The hydrophilic component layer is not particularly limited as long as it contains a hydrophilic component(s). Examples of the hydrophilic component include components such as saccharides, water-soluble polymers, surfactants, colloid particles, and inorganic particles. The hydrophilic component layer may contain one kind of hydrophilic component alone, or two or more kinds of hydrophilic components, for example. Examples of the saccharides include sucrose, N-methyl glucosamine, glucose, fructose, maltose, and lactose. Among them, sucrose and N-methyl glucosamine are particularly preferable. Examples of the water-soluble polymers include polyvinyl alcohol, polyvinyl pyrrolidone, and polyethylene glycol. Examples of the surfactants include polyoxyethylene sorbitan alkyl ester (e.g., a Tween series surfactant), polyoxyethylene-p-t-octylphenyl ether (e.g., a Triton series surfactant), and sodium dodecyl sulfate (SDS). Examples of the colloid particles include gold colloid particles, ferric hydroxide colloid particles, and silver colloid particles. Examples of the inorganic particles include silica powder, alumina, titania, calcium carbonate, and magnesium carbonate.

The immobilized antibody is not particularly limited as long as it is an antibody that binds to an antigen as an analyte in a sample. The antibody can be set as appropriate depending on an antigen and the like to be described below. The antibody may be derived from a living organism or synthesized artificially, for example. Examples of the antibody derived from a living organism include immunogloblins (Ig), antibody fragments, and chimeric antibodies. Examples of the immunogloblins include IgG, IgA, IgM, IgE, and IgD. Examples of the antibody fragments include Fab, Fab', and F(ab')2. Examples of the chimeric antibodies include humanized antibodies. The antibody may be derived from animal species such as mammals like mice, rabbits, cows, pigs, horses, sheep, and goats; birds such as chickens; and humans, for example, and are not particularly limited. The antibody may be produced from serum derived from any of the above-described animal species by a conventionally known method, or any of various kinds of commercially available antibodies may be used as the antibody, and they are not particularly limited. As the antibody, either of a polyclonal antibody and a monoclonal antibody may be used, for example. Examples of the artificially-synthesized antibodies include affibodies. A method for immobilizing the antibody in the detection portion may be such that, for example, applying an antibody solution containing the antibody to the development member such as a porous membrane using an applicator, and then air drying the solution using a dryer or the like.

Examples of the material of the plastic case include polyethylene, polystyrene, polypropylene, and synthetic resins obtained by copolymerization of acrylonitrile, butadiene, and styrene. Preferably, the plastic case contains a hydrophobic component(s). The hydrophobic component is, for example, a lubricant, a plasticizer, a release agent, a stabilizer, an antioxidant, or the like. The shape and the size of the plastic case are not particularly limited, and can be set as appropriate depending on the shape and the size of the development member and the like, for example.

The sample analysis tool of the present invention preferably is produced by the production method of the present invention, although the production method is not particularly limited. Furthermore, in the production method of the present invention, the respective steps may be performed either sequentially or simultaneously. In the following, an example of a method for producing the sample analysis tool according to the present embodiment will be described with reference to FIG. 1.

The hydrophilic component layer 15 is formed on part or the whole of the surface of the developing solution supply portion 12 in the development member 11. The hydrophilic component layer is formed in the following manner, for example. Specifically, first, a solution, a suspension, or the like containing the hydrophilic component(s) is prepared. The concentration of the hydrophilic component(s) in the solution or the like is in the range from 0.1 to 10 wt %, preferably from 0.5 to 7.5 wt %, and more preferably from 1 to 5 wt %, for example. The solution or the like can be prepared by dissolving or suspending the hydrophilic component(s) in a solvent, for example. The solvent may be water, a buffer, or the like, for example. The buffer is not particularly limited, and examples thereof include buffers to be described below. Then, the hydrophilic component layer is formed by applying the solution containing the hydrophilic component(s) to the development member using, for example, an applicator or like, and then air drying the solution using a dryer or the like. In this state, the development member 11 is disposed in the plastic case 16. At this time, the development member 11 is disposed so that the lower end of the developing solution supply port 17 is in contact with the development member 11 (the developing solution supply portion 12) via the hydrophilic component layer 15. The sample analysis tool of the present embodiment shown in FIG. 1 can be produced in the above-described manner. It is to be noted, however, the method for producing the sample analysis tool according to the present embodiment is not limited to this illustrative example. The plastic case 16 and the development member 11 each may be a commercially available product or may be self-produced.

Next, an enzyme immunoassay method using the sample analysis tool of the present embodiment is performed using a sample solution, an enzyme-labeled antibody, a developing solution, a substrate, and the like, for example.

The sample solution is not particularly limited as long as it contains a sample. The sample is not particularly limited, and examples thereof include biological samples and food. The sample may be in the form of liquid, or the sample in the form of solid may be, for example, dissolved, suspend, or dispersed in a buffer or the like. Examples of the liquid biological sample include nasal aspirate, nasal lavage fluid, nasal swab, nasal secretion, throat swab, oral rinse, saliva, whole blood, serum, plasma, sweat, and urine. Examples of the solid biological sample include cells and feces. Examples of the food include: food substances such as animals and plants; and processed food. The buffer is not particularly limited, and examples thereof include a Tris buffer, a phosphate buffer, an acetic acid buffer, and a boric acid buffer. The pH of the buffer is not particularly limited, and is in the range from 4 to 10, preferably from 6 to 9, for example.

In the immunoassay method, an analyte in the sample is an antigen that binds to the above-described immobilized antibody or a labeled antibody to be described below. Examples of the antigen include, but not particularly limited to: biogenic substances including pathogen antigens, antibodies, cancer markers, and hormones, such as influenza A viruses, influenza B viruses, influenza C viruses, adenoviruses, RS viruses, coronaviruses, astroviruses, noroviruses, measles viruses, rotaviruses, human immunodeficiency viruses (HIV), human T-cell leukemia viruses (HTLV-1), hepatitis B viruses (HBV), hepatitis C viruses (HCV), herpesviruses, *Mycoplasma, Treponema pallidum, Chlamydia trachomatis,* tubercle bacilli, coliform bacteria, group A streptococci, group B streptococci, *Streptococcus pneumoniae,* staphylococci, MRSA, *Legionella,* enterohemorrhagic *Escherichia coli* O157, verotoxin, *Salmonella, Clostridium difficile, Helicobacter pylori,* CRP, HBs antigens, HBs antibodies, HBc antigens, HBc antibodies, HBe antigens, HBe antibodies, prostate-specific antigens (PSA), human chorionic gonadotrophin (hCG), luteinizing hormone (LH), troponin T, troponin I, myoglobin, D-dimer, fecal hemoglobin, hemoglobin A1c, and IgE antibodies; residual agricultural chemicals; environment hormones; and allergic substances in food.

The sample solution may contain a buffer, a surfactant, an antibacterial agent, and the like, for example. The buffer is not particularly limited, and examples thereof include the above-described buffers. The surfactant is not particularly limited, and examples thereof include anionic surfactants, nonionic surfactants, and amphoteric surfactants. The antibacterial agent is not particularly limited, and examples thereof include sodium azide, 5-chloro-2-methyl-4-isothiazoline-3-one, and 2-methyl-4-isothiazoline-3-one.

The enzyme-labeled antibody is not particularly limited as long as it is an enzyme-labeled antibody that binds to an antigen as an analyte in the sample. The antibody of the enzyme-labeled antibody is, for example, an antibody to any of the above-described various antigens and the like, and can be set as appropriate depending on the antigen and the like. Examples of the antibody include those described above as examples of the antibody of the immobilized antibody.

The enzyme of the enzyme-labeled antibody is not particularly limited, and examples thereof include peroxidase, alkaline phosphatase, and β-D-galactosidase. The method for preparing the enzyme-labeled antibody is not particularly limited, and a conventionally known method may be used, for example.

The enzyme-labeled antibody may be contained in the sample solution previously, or the development member, a pad provided additionally, or the like may be impregnated with the enzyme-labeled antibody previously, for example. However, for example, since it is possible to perform analysis with higher sensitivity without providing the pad or the like additionally, it is preferable that the enzyme-labeled antibody is contained in the sample solution previously.

As the developing solution, a Tris buffer, a phosphate buffer, an acetic acid buffer, a boric acid buffer, or the like may be used, for example. To the developing solution, a stabilizer, an antibacterial agent, and the like may be added as appropriate, for example. Furthermore, the amount of the developing solution to be supplied can be set as appropriate depending on the amount of the sample solution to be supplied and the like, for example.

The substrate is not particularly limited, and the one that develops color or emits light, for example, when reacting with the enzyme is preferable, for example. The kind of the substrate is not particularly limited, and can be selected depending on the kind of the enzyme used in the enzyme-labeled antibody, for example. Specific examples of the substrate include 2,2'-azino-bis(3-ethylbenzothiazoline-6-sulfonic acid) (ABTS), 3,3',5,5'-tetramethylbenzidine (TMB), diaminobenzidine (DAB), 5-bromo-4-chloro-3-indolylphosphate (BCIP), 4-methylumbelliferyl-β-D-galactoside (4MUG), and 3-(2'-spiroadamantane)-4-methoxy-4-(3"-β-D-galactopyranosyl)phenyl-1,2-dioxetane (AMGPD).

By the development of the developing solution, the substrate can be introduced to the detection portion from the developing solution supply portion via the sample supply portion, for example. At this time, the substrate may be contained in the developing solution previously; the substrate may be contained in the sample solution previously; or the development member or the like may be impregnated with the substrate, for example. When impregnating the development member or the like with the substrate, a portion between the sample supply portion and the detection portion or a portion between the developing solution supply portion and the sample supply portion in the development member may be impregnated with the substrate.

Next, the immunoassay method in the present embodiment will be described specifically with reference to FIG. 3.

Figure 3A:
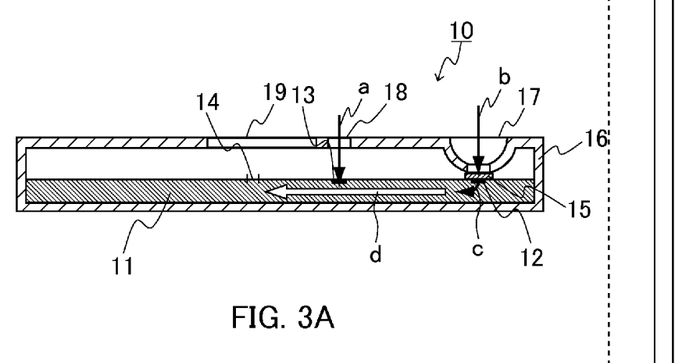
FIG. 3A is a sectional view for illustrating an immunoassay method in the embodiment of the present invention.
Figure 3B:
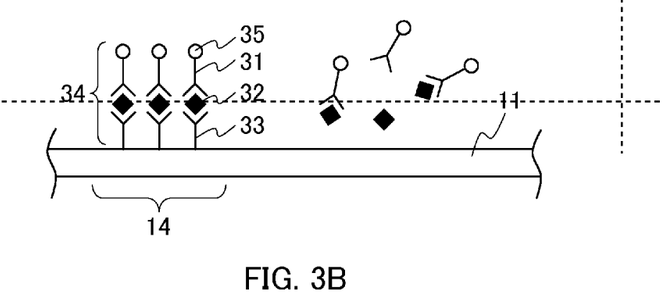
FIG. 3B is a schematic view for illustrating the detection of an antigen in a detection portion.

FIG. 3A is a sectional view of the sample analysis tool. FIG. 3B is a schematic view for illustrating the detection of an antigen in a detection portion.

First, as shown in FIG. 3A, the sample solution is supplied to the sample supply portion 13 through the sample supply port 18 (the arrow a). The enzyme-labeled antibody may previously be mixed in the sample solution before being supplied, or a portion in the vicinity of the sample supply portion 13 in the development member 11 may be impregnated with the enzyme-labeled antibody previously. Next, through the developing solution supply port 17, the developing solution is supplied to the developing solution supply portion 12 whose surface is entirely covered with the hydrophilic component layer 15 (the arrow b). At this time, because the surface of the developing solution supply portion 12 is entirely covered with the hydrophilic component layer 15, the supplied developing solution permeates the development member 11 rapidly as indicated with the arrow c without being adversely affected by the hydrophobic component(s) derived from the plastic case 16 and while dissolving the hydrophilic component(s) in the hydrophilic component layer 15. The developing solution having permeated the development member 11 develops from upstream to downstream of the development member 11 toward the detection portion 14 (to the left in FIG. 3A) in the development member 11, as indicated with the arrow d. At this time, in the case where a portion in the vicinity of the developing solution supply portion 12 in the development member 11 is previously impregnated with the above-described substrate, the substrate moves toward the detection portion 14 by the development of the developing solution. The substrate may previously be mixed in the developing solution before being supplied. In the above-described manner, in the development member 11, the developing solution develops (the arrow d) in the presence of the labeled antibody, whereby the substrate, the sample solution, and the enzyme-labeled antibody are introduced to the detection portion 14 on which the antibody 33 has been immobilized. As shown in FIG. 3B, in the detection portion 14, a complex 34 of the immobilized antibody 33, the antigen 32 as the analyte in the sample, and the enzyme-labeled antibody 31 is formed. Then, the enzyme 35 contained in the complex 34 reacts with the substrate, which also has been introduced to the detection portion 14, whereby color is developed or light is emitted, for example. Thus, in the detection portion 14, the color development, light emission, or the like caused by the reaction between the enzyme 35 and the substrate is detected through observation via the window 19. This allows the antigen 32 to be detected (quantitative analysis, semi-quantitative analysis, qualitative analysis, or the like) indirectly. The detection may be performed by determination through visual observation or may be performed with the use of a colorimeter, a fluorometer, a photon counter, a photosensitive film, or the like, for example.

In the present embodiment, the sample analysis tool may further includes, for example, a developing solution receiving pad and a waste liquid absorbing pad, in order to accelerate the development of the developing solution. Also, the sample analysis tool may further include a support in order to maintain the shape of the sample analysis tool stably, for example. Specifically, for example, by disposing the development member, the developing solution receiving pad, the waste liquid absorbing pad, and the like on the support, the respective components in the sample analysis tool can be supported.

The materials of the developing solution receiving pad and the waste liquid absorbing pad are not particularly limited, and examples thereof include polyethylene, glass fiber, rayon, nylon, paper, and cellulose. The shape and the size of the developing solution receiving pad are not particularly limited, and can be set as appropriate depending on the shape and the like of the development member, for example.

The material of the support is not particularly limited, and examples thereof include polyethylene terephthalate, polyethylene, polystyrene, polyester, and cellulose acetate. The shape of the support is not particularly limited, and examples thereof include a film-like shape, a sheet-like shape, and a plate-like shape. The shape and the size of the support are not particularly limited, and can be set as appropriate depending on the development member and the like.

The development member, the developing solution receiving pad, and the waste liquid absorbing pad can be disposed on the support by an ordinary method, for example. Specifically, for example, they may be fixed on the support using a two-sided tape, an adhesive, or the like.

Figure 4:
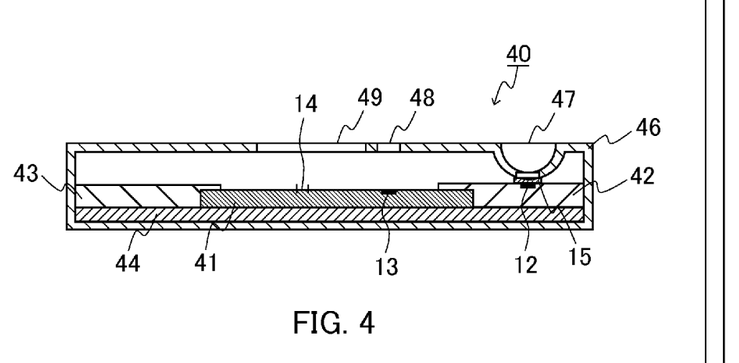
FIG. 4 is a sectional view showing another example of the configuration of the sample analysis tool according to the embodiment of the present invention.

FIG. 4 is a sectional view showing another example of the configuration of the sample analysis tool of the present embodiment. As shown in FIG. 4, this sample analysis tool 40 includes, as main components, a development member 41, a developing solution receiving pad 42, a waste liquid absorbing pad 43, a support 44, and a plastic case 46. The developing solution receiving pad 42 is disposed so as to be adjacent to the upstream side of the development member 41 (the right side in FIG. 4). The waste liquid absorbing pad 43 is disposed so as to be adjacent to the downstream side of the development member 41 (the left side in FIG. 4) with respect to the detection portion 14. The development member 41, the developing solution receiving pad 42, and the waste liquid absorbing pad 43 are contained in the plastic case 46 in the state of being disposed on the support 44. The plastic case 46 includes a developing solution supply port 47, a sample supply port 48, and a window 49. In this sample analysis tool 40, the developing solution supply portion 12 is provided on the developing solution receiving pad 42 disposed so as to be adjacent to the upstream side of the development member 41 (the developing solution receiving pad 42 is integrated with the development member 41). The hydrophilic component layer 15 is formed so as to cover the surface of this developing solution supply portion 12 entirely. In the present embodiment, the developing solution supply portion 12 is a predetermined region in the developing solution receiving pad 42. Except for the above, this sample analysis tool 40 has the same configuration as the above-described sample analysis tool 10.

In an immunoassay method using this sample analysis tool 40, the developing solution is supplied to the developing solution receiving pad 42 through the developing solution supply port 47. Except for this, the immunoassay method can be carried out in the same manner as the above-described immunoassay method. Furthermore, as described above, the substrate may be contained in the developing solution previously, or the developing solution receiving pad 42 may be impregnated with the substrate previously, for example.

In the present embodiment, in the case where the analyte in the sample is an antibody, the sample analysis tool may be configured so that, for example, the detection portion includes an immobilized antigen instead of the immobilized antibody. With this configuration, a complex of the enzyme-labeled antibody or enzyme labeled antigen, the antibody as the analyte in the sample, and the immobilized antigen is formed, and the enzyme contained in the complex reacts with the substrate, whereby color is developed or light is emitted, for example. By detecting this color development, light emission, or the like, it is possible to detect the antibody indirectly. The antibody as the analyte in the sample is not particularly limited, and examples thereof include various kinds of antibodies. An antigen of the immobilized antigen is not particularly limited as long as it can bind to the antibody as the analyte in the sample. An antibody of the enzyme-labeled antibody is not particularly limited as long as it can bind to the antibody as the analyte in the sample. Also, an antigen of the enzyme labeled antigen is not particularly limited as long as it can bind to the antibody as the analyte in the sample. As a method for preparing the antibody of the enzyme-labeled antibody and a method for labeling the antibody, conventionally known methods can be used, and examples of the enzyme to be used are the same as those described above. Also, as a method for preparing the antigen of the enzyme-labeled antigen and a method for labeling the antigen, conventionally known methods can be used, and examples of the enzyme to be used are the same as those described above. A method for producing the immobilized antigen may be, for example, a conventionally known method or the like, and is not particularly limited. Also, a method for immobilizing the immobilized antigen to the detection portion may be, for example, a conventionally known method or the like, and is not particularly limited.

Second Embodiment

A sample analysis tool according to the present embodiment is a sample analysis tool for use in an immunoassay method in which colored insoluble carrier particles are used as a label of a labeled antibody.

The colored insoluble carrier particles are not particularly limited, and examples thereof include colored latex particles, metal colloid particles, colored polymethyl methacrylate particles, colored polylactic acid particles, colored porous glass particles, colored silica particles, colored agarose particles, and colored dextran particles. The colored latex particles are not particularly limited, and examples thereof include blue latex particles and red latex particles. The metal colloid particles are not particularly limited, and examples thereof include gold colloid particles and platinum colloid particles.

The method for labeling an antibody with the colored insoluble carrier particle is not particularly limited. For example, the labeled antibody can be prepared by suspending the colored insoluble carrier particles in a buffer or the like, and adding the antibody to this suspension so as to cause a reaction between them. The buffer is not particularly limited, and examples thereof include the above-described buffers.

In the present invention, for example, the labeled antibody having the colored insoluble carrier particles bound thereto may be contained in the sample solution previously, or the development member, a pad provided additionally, or the like may be impregnated with the labeled antibody having the colored insoluble carrier particles bound thereto, for example. However, for example, since it is possible to perform analysis with higher sensitivity without providing the pad or the like additionally, it is preferable that the labeled antibody having the colored insoluble carrier particles bound thereto is contained in the sample solution.

Next, an immunoassay method in the present embodiment will be described. In the present embodiment, by detecting coloring caused by the agglutination of the colored insoluble carrier particles in the detection portion, the antigen is detected (quantitative analysis, semi-quantitative analysis, qualitative analysis, or the like) indirectly. In the present embodiment, no substrate is used. The detection may be performed by determination through visual observation or may be performed with the use of colorimeter or the like, for example. Except for this, the immunoassay method can be carried out in the same manner as the immunoassay method in the first embodiment.

Third Embodiment

A sample analysis tool according to the present embodiment is a sample analysis tool for use in an immunoassay method in which a fluorescent dye is used as a label of a labeled antibody.

The fluorescent dye is not particularly limited, and examples thereof include FITC. When an antibody or antigen labeled with a fluorescent dye is used, for example, a complex of the immobilized antibody, an antigen as the analyte, and the labeled antibody, or a complex of the immobilized antigen, an antibody as an analyte, and the labeled antibody or labeled antigen is formed, and light emitted by the fluorescent dye in the labeled antibody or labeled antigen can be detected by irradiating the complex with excitation light.

Fourth Embodiment

A sample analysis tool according to the present embodiment is a sample analysis tool for use in an analysis method in which a sample solution is caused to react with a reagent contained in a reagent layer.

Figure 5A:
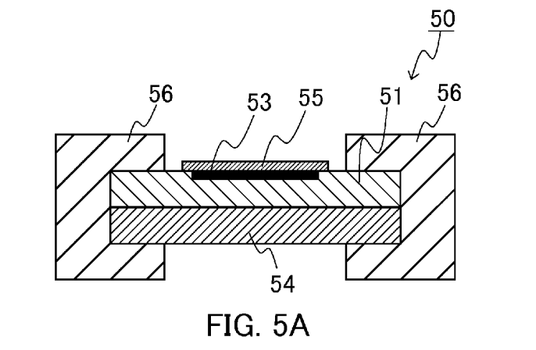
FIG. 5 shows sectional views showing an example of the configuration of a sample analysis tool according to another embodiment of the present invention.
Figure 5B:
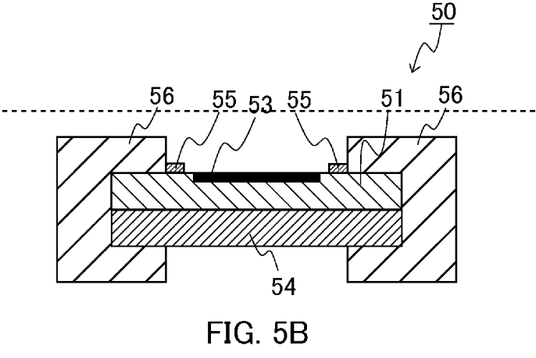
Figure 5C:
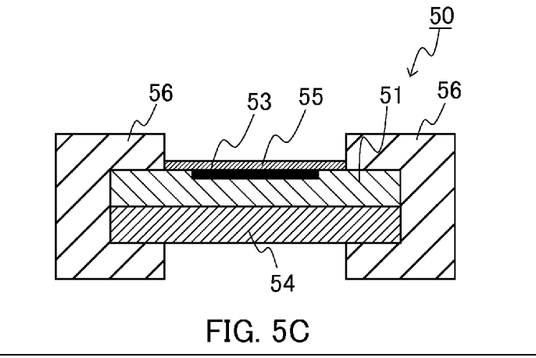

FIG. 5A is a sectional view showing an example of the configuration of the sample analysis tool of the present embodiment. As shown in FIG. 5A, this sample analysis tool 50 includes a development member 51 including a sample supply portion 53, a reagent layer 54, and a pair of plastic bases 56. The reagent layer 54 is disposed on a surface of the development member 51 on the side opposite to the sample supply portion 53 side. The pair of plastic bases 56 holds the development member 51 and the reagent layer 54 therebetween. A hydrophilic component layer 55 is formed so as to cover the surface of the sample supply portion 53 entirely. With this configuration, in the sample analysis tool of the present embodiment, it is possible to prevent the adhesion of a hydrophobic component(s) derived from the plastic bases to the sample supply portion. As a result, the sample analysis tool according to the present embodiment also can exhibit the effect of the present invention. It is to be noted that the sample analysis tool of the present embodiment is not limited to this illustrative example. For example, as shown in the sectional view of FIG. 5B, the sample analysis tool may be configured so that the hydrophilic component layers 55 are formed in contact portions of the development member 51 with the pair of plastic bases 56. Also with such a configuration, it is possible to prevent the adhesion of the hydrophobic component(s) derived from the plastic bases to the sample supply portion. Furthermore, as shown in the sectional view of FIG. 5C, the sample analysis tool of the present embodiment also may be configured so that, for example, the hydrophilic component layer 55 is formed on both the sample supply portion 53 and the above-described contact portions. Also with such a configuration, it is possible to prevent the adhesion of the hydrophobic component(s) derived from the plastic base to the sample supply portion. Although the sample analysis tool of the present embodiment includes the pair of plastic bases 56, the present invention is not limited to this illustrative example. For instance, a plastic base may be formed in a different shape so as to have portions for holding the development member and the reagent layer therebetween.

The development member and the hydrophilic component layer are the same as those described above.

The reagent layer is obtained by, for example, impregnating a porous member with a reagent and then drying the porous member. As the porous member, a conventionally known porous member can be used. The kind of the reagent used for the impregnation can be determined as appropriated depending on an analyte in a sample, which will be described below.

The material of the pair of plastic bases is not particularly limited, and examples thereof include the same materials as descried above as examples of the material of the plastic case or the support. In this sample analysis tool 50, the pair of plastic bases 56 has shapes so as to hold the development member 51 and the reagent layer 54 therebetween. However, the shapes of the plastic bases are not particularly limited. For example, the plastic bases each may have a film-like shape, a sheet-like shape, or a plate-like shape. Alternatively, they may have shapes such that they are laminated on the development member 51 and the reagent layer 54, respectively, so as to support the development member 51 and the reagent layer 54.

Sample analysis using the sample analysis tool of the present embodiment can be carried out in the following manner. First, a sample solution is supplied to the sample supply portion 53. At this time, because the surface of the sample supply portion 53 is covered with the hydrophilic component layer 55 entirely, the supplied sample solution permeates the development member 51 rapidly without being adversely affected by the hydrophobic component(s) derived from the plastic bases 56 and while dissolving the hydrophilic component(s) in the hydrophilic component layer 55. Then, when the sample solution comes into contact with the reagent layer 54, an analyte in the sample solution reacts with the reagent, whereby color development, change in color tone, or the like is caused. The detection of the color development, change in color tone, or the like may be performed by determination through visual observation or may be performed with the use of a colorimeter or the like.

The sample solution is not particularly limited as long as it contains a sample. Examples of the analyte in the sample include glucose, cholesterol, triglyceride, ammonia, uric acid, creatinine, urea nitrogen, calcium, inorganic phosphorus, magnesium, GGT, GOT, GPT, LDH, amylase, total protein, albumin, fructosamine, creatine phosphokinase, bilirubin, alkaline phosphatase, and HDL.

EXAMPLES

Next, examples of the present invention will be described together with comparative examples. It is to be noted, however, the present invention is by no means limited or restricted by the following examples and comparative examples.

Example 1

(Production of Sample Analysis Tool)

A sample analysis tool 40 having the configuration shown in FIG. 4 was produced in the following manner. Specifically, first, a porous member made of nitrocellulose and having a length of 50 mm, a width of 4 mm, and a thickness of 5 µm was provided as a development member 41; a porous member made of glass fiber and having a length of 20 mm, a width of 4 mm, and a thickness of 0.5 mm was provided as a developing solution receiving pad 42; a porous member made of cellulose and having a length of 25 mm, a width of 4 mm, and a thickness of 1.5 mm was provided as a waste liquid absorbing pad 43; and a backing sheet (PET) having a length of 80 mm and a width of 4 mm was provided as a support 44. At a distance of 30 mm from one end of the development member 41 (the right end in FIG. 4), an aqueous solution of a protein extracted from egg white allergen (the aqueous solution obtained by diluting the protein with a 1 mg/ml (5 mmol/l) boric acid buffer (pH 8.5) and then dialyzing it) was applied so as to form a line with a width of 1 mm. Thus, a detection portion 14 was formed on a surface of the development member 41. Furthermore, at a distance of 10 mm from one end of the developing solution receiving pad 42 (the right end in FIG. 4), 50 of 5-bromo-4-chloro-3-indolyl phosphate (20 mg/ml, Boehringer Mannheim, trade name "BCIP") was applied as a substrate, and allowed to stand at 37° C. for 1 hour so as to be dried. Subsequently, 160 of a 1 wt % aqueous solution of sucrose was applied so as to cover the developing solution supply portion 12 of the developing solution receiving pad 42 entirely (the area of applied portion: 4 to 8 mm$^2$) using an applicator, and then dried. Thus, a hydrophilic component layer 15 was formed on the developing solution receiving pad 42. These members were contained in a plastic case 46, as shown in FIG. 4. Thus, the sample analysis tool 40 of the present example was produced. Then, the sample analysis tool 40 of the present example was stored at 60° C. for 1 week.

Example 2

A sample analysis tool 40 of the present example was produced in the same manner as in Example 1, except that 16 µl of a 5 wt % aqueous solution of sucrose was applied.

Example 3

A sample analysis tool 40 of the present example was produced in the same manner as in Example 1, except that 16 µl of a 5 wt % aqueous solution of N-methyl glucosamine was applied.

Example 4

A sample analysis tool 40 of the present example was produced in the same manner as in Example 1, except that 16 µl of a 1 wt % aqueous solution of sodium dodecyl sulfate (SDS) was applied.

Example 5

A sample analysis tool 40 of the present example was produced in the same manner as in Example 1, except that 16 µl of a 1 wt % aqueous solution of polyvinyl pyrrolidone was applied.

Comparative Example 1

A sample analysis tool according to the present comparative example was produced in the same manner as in Example 1, except that the hydrophilic component layer 15 was not formed.

Comparative Example 2

A sample analysis tool according to the present comparative example was produced in the same manner as in Example 1, except that 16 µl of water was applied.

(Immunoassay Using Sample Analysis Tool)

(1) Preparation of Sample Solution

A sample solution was prepared by adding 10 µl of egg white-specific IgE positive serum and 60 µl of alkaline phosphatase-labeled antibody (enzyme-labeled antibody, 10 µg, derived from a goat) to 50 mmol/l Tris-HCl buffer (pH: 7.4).

(2) Preparation of Developing Solution 100 mmol/l sodium carbonate/sodium hydrogencarbonate buffer (pH: 10.0) was prepared. This buffer was used as a developing solution.

(3) Carrying Out Immunoassay Method

An immunoassay method was carried out in the following manner using each of the sample analysis tools of the examples and the comparative examples. Specifically, first, 10 µl of the sample solution was supplied to the sample supply portion 13 through the sample supply port 48. Next, 100 µl of the developing solution was supplied to the developing solution supply portion 12 through the developing solution supply port 47.

(Evaluation of Permeability to Developing Solution)

1 minute and 20 minutes after the supply of the developing solution, the developing solution supply portion 12 was observed visually, and the permeability to the developing solution was evaluated according to the following evaluation criteria.

Evaluation Criteria of Permeability to Developing Solution

G: The developing solution had permeated completely.
NG: The developing solution had not permeated completely and some of it remained.

(Immunoassay Evaluation)

20 minutes after the supply of the developing solution, a coloring line in the detection portion 14 was analyzed using an immunoassay device (ARKRAY, Inc., trade name "SPOTCHEM IL SL-4720"). This immunoassay device displays an analysis result as a numerical value from 0 to 6 or "E", depending on the density of the coloring line. When a numerical value from "2 to 6" is displayed, it means a coloring line is detected and the analysis result is positive (+). On the other hand, when a numerical value of "0 or 1" or "E" is displayed, no coloring line is detected and the analysis result is negative (−).

The evaluation results obtained in the respective examples are shown in Table 1 below. The evaluation results obtained in the respective comparative examples are shown in Table 2 below.

TABLE 1

| Evaluation of permeability | Ex. 1 | Ex. 2 | Ex. 3 | Ex. 4 | Ex. 5 |
|---|---|---|---|---|---|
| After 1 minute | G | G | G | G | G |
| After 20 minutes | G | G | G | G | G |
| Immunoassay evaluation | + | + | + | + | + |
| (Display on the device) | (3) | (3) | (3) | (3) | (3) |

TABLE 2

| Evaluation of permeability | Comp. Ex. 1 | Comp. Ex. 2 |
|---|---|---|
| After 1 minute | NG | NG |
| After 20 minutes | NG | NG |
| Immunoassay evaluation | − | − |
| (Display on the device) | (E) | (E) |

As can be seen from Table 1, in the sample analysis tools 40 according to Examples 1 to 5 each provided with the hydrophilic component layer 15, the developing solution had permeated the development member 11 after 1 minute from the supply of the developing solution. Thus, the permeability to the developing solution was favorable. Furthermore, in the immunoassay evaluation, the analysis results were all positive. In contrast, as can be seen from Table 2, in the sample analysis tool of Comparative Example 1 having no hydrophilic component layer 15 and in the sample analysis tool of Comparative Example 2 to which water was applied, even after 20 minutes from the supply of the developing solution, the developing solution had not permeated the development member 11 and remained in the form of water droplets on the developing solution supply portion 12. That is, the permeability to the developing solution was poor. Furthermore, in the immunoassay evaluation, the analysis results were both negative.

INDUSTRIAL APPLICABILITY

As specifically described above, according to the present invention, the reproducibility and reactivity in analysis can be prevented from decreasing. The present invention can be used suitably in the detection (quantitative analysis, semi-quantitative analysis, qualitative analysis, or the like) of a specific substance contained in whole blood, serum, plasma, saliva, urine, spinal fluid, or the like, for example. Furthermore, the present invention is applicable to fields such as clinical tests, biochemical tests, and medical research. The use of the present invention is not limited, and the present invention can be applied to a wide range of fields.

EXPLANATION OF REFERENCE NUMERALS 10, 40, 50, 60: sample analysis tool
11, 41, 51, 61: development member
12, 62: developing solution supply portion
13, 53, 63: sample supply portion
14, 64: detection portion
15, 55: hydrophilic component layer
16, 46, 66: plastic case
17, 47, 67: developing solution supply port
18, 48, 68: sample supply port
19, 49, 69: window
31: enzyme-labeled antibody
32: antigen
33: immobilized antibody
34: complex
35: enzyme
42: developing solution receiving pad
43: waste liquid absorbing pad
44: support
54: reagent layer
56: pair of plastic bases
a, b, c, d: arrow

The invention claimed is:
1. A sample analysis tool comprising:
a plastic base including a developing solution supply port and a sample supply port that is apart from the developing solution supply port;
a development member that has a porous structure capable of exhibiting a capillary action, a surface of the development member comprising:
  a developing solution supply portion, that is a region configured to receive a developing solution supplied from outside through the developing solution supply port to let the developing solution permeate the development member;
  a sample supply portion, that is a region apart from the developing solution supply portion and that is configured to receive a sample solution containing an analyte supplied from outside through the sample supply port to let the sample solution permeate the development member; and
  a detection portion, that is a region apart from the developing solution supply portion and the sample supply portion, and that is a region in which a substance that specifically binds to the analyte is immobilized, wherein the developing solution supply portion, the sample supply portion and the detection portion being arranged in this order; and
a hydrophilic component layer disposed between a contact surface of the developing solution supply portion and a contact surface of the developing solution supply port,
wherein the contact surface of the developing solution supply portion directly contacts the hydrophilic com- ponent layer, and the contact surface of the developing solution supply port directly contacts the hydrophilic component layer, and wherein the hydrophilic component layer comprises at least one component selected from the group consisting of saccharides, water-soluble polymers, surfactants, colloid particles, and inorganic particles.

2. The sample analysis tool according to claim 1, wherein a contact surface of the development member contacting the plastic base includes the developing solution supply portion.

3. The sample analysis tool according claim 1, wherein the hydrophilic component layer contains a nonvolatile hydrophilic component.

4. The sample analysis tool according to claim 1, wherein the hydrophilic component layer comprises saccharides, and the saccharides include at least one selected from the group consisting of sucrose and N-methyl glucosamine.

5. The sample analysis tool according to claim 1, wherein the plastic base comprises a plastic case, and the development member is disposed in the plastic case.

6. The sample analysis tool according to claim 1, wherein the developing solution supply portion, the sample supply portion, and the detection portion are provided in this order from upstream to downstream along a flow of the developing solution, wherein the supplied sample solution is introduced to the detection portion by development of the supplied developing solution in the development member in the presence of a labeled substance that specifically binds to the analyte, wherein a complex comprising the immobilized substance that specifically binds to an analyte, the analyte, and the labeled substance that specifically binds to an analyte is formed in the detection portion, and wherein the sample analysis tool is configured to analyze the analyte by detecting the label in the complex.

7. The sample analysis tool according to claim 6, wherein the immobilized substance that specifically binds to the analyte and the labeled substance that specifically binds to the analyte each are an antigen or an antibody.

8. The sample analysis tool according to claim 1, wherein the plastic base is configured to hold the development member in a sandwiched manner.

9. The sample analysis tool according to claim 8, further comprising:
a reagent layer,
wherein the plastic base is configured to hold the development member and the reagent layer in a sandwiched manner.

10. The sample analysis tool according to claim 1, wherein
the plastic base comprises a hydrophobic component.

11. A method for producing a sample analysis tool comprising:
providing a plastic base including a developing solution supply port and a sample supply port that is apart from the developing solution supply port, and a development member that has a porous structure capable of exhibiting a capillary action, a surface of the development member comprising:
a developing solution supply portion, that is a region configured to receive a developing solution supplied from outside through the developing solution supply port to let the developing solution permeate the development member;
a sample supply portion, that is a region apart from the developing solution supply portion and that is configured to receive a sample solution containing an analyte supplied from outside through the sample supply port to let the sample solution permeate the development member; and
a detection portion, that is a region apart from the developing solution supply portion and the sample supply portion, and that is a region in which a substance that specifically binds to the analyte is immobilized, wherein the developing solution supply portion, the sample supply portion and the detection portion being arranged in this order; and
forming a hydrophilic component layer between a contact surface of the developing solution supply portion and a contact surface of the developing solution supply port,
wherein the contact surface of the developing solution supply portion directly contacts the hydrophilic component layer, and the contact surface of the developing solution supply port directly contacts the hydrophilic component layer, and
wherein the hydrophilic component layer comprises at least one component selected from the group consisting of saccharides, water-soluble polymers, surfactants, colloid particles, and inorganic particles.

12. The method according to claim 11, wherein
the hydrophilic component layer is formed on at least a portion of a surface of the sample supply portion.

13. The method according to claim 12, wherein
a contact surface of the development member contacting the plastic base includes the developing solution supply portion.

14. A method for inhibiting a decrease in liquid permeability of a development member in a sample analysis tool comprising:
providing a plastic base including a developing solution supply port and a sample supply port that is apart from the developing solution supply port, and a development member that has a porous structure capable of exhibiting a capillary action, a surface of the development member comprising:
a developing solution supply portion, that is a region configured to receive a developing solution supplied from outside through the developing solution supply port to let the developing solution permeate the development member;
a sample supply portion, that is a region apart from the developing solution supply portion and that is configured to receive a sample solution containing an analyte supplied from outside through the sample supply port to let the sample solution permeate the development member; and
a detection portion, that is a region apart from the developing solution supply portion and the sample supply portion, and that is a region in which a substance that specifically binds to the analyte is immobilized, wherein the developing solution supply portion, the sample supply portion and the detection portion being arranged in this order; and
forming a hydrophilic component layer between a contact surface of the developing solution supply portion and a contact surface of the developing solution supply port,
wherein the contact surface of the developing solution supply portion directly contacts the hydrophilic component layer and the contact surface of the plastic bascdeveloping solution supply port directly contacts the hydrophilic component layer, and wherein the hydrophilic component layer comprises at least one component selected from the group consisting of saccharides, water-soluble polymers, surfactants, colloid particles, and inorganic particles; and preventing the hydrophobic component from adhering to the development member by the hydrophilic component layer, thereby inhibiting the decrease in liquid permeability of the development member.

15. The method according to claim 14, wherein at least a portion of the developing solution supply portion is in contact with the plastic base.

* * * * *